United States Patent [19]
Hubbes

[11] Patent Number: 6,160,100
[45] Date of Patent: Dec. 12, 2000

[54] TREATMENT FOR WILT DISEASES OF TREES

[76] Inventor: Martin Hubbes, 24 Roywood Drive, Toronto, Ontario, Canada, M3A 2C6

[21] Appl. No.: 09/160,246

[22] Filed: Sep. 25, 1998

Related U.S. Application Data

[63] Continuation-in-part of application No. 09/048,052, Mar. 26, 1998.
[60] Provisional application No. 60/041,630, Mar. 27, 1997.

[51] Int. Cl.⁷ .................................................. C07K 14/37
[52] U.S. Cl. ......................... 530/395; 530/322; 530/371; 514/8; 800/200
[58] Field of Search ............................. 800/200; 530/322, 530/371, 395; 514/8

[56] References Cited

PUBLICATIONS

Dumas et al., "Isolation and identification of six mansonones from *Ulmus americana* . . . ", Experientia 39 (1983) pp. 1089–1090.
Hubbes, "Pathogen Virulence and Host Reaction in Dutch Elm Disease", Naturaliste can. (Rev. Écol. Syst.), 115: 157–161 (1988).
Yang et al., "Factors influencing mansonone induction in elm cells . . . ", Eur. J. For. Path. 23 (1993) 257–268.
Yang et al., "Mansonone accumulation in elm cellus induced by . . . ", Can. J. Bot. vol. 67, 1989, pp. 3490–3497.
Jeng et al., "Mitochondrial DNA restriction fragment length . . . ", Mycol. Res. 95(5): 537–542 (1991).
Hubbes, "Influence of biotechnology on forest disease research and . . . ", Canadian Journal of Plant Pathology 9: 343–348, 1987.
Hubbes, "Terpenes and unsaturated fatty acids trigger coremia . . . ", Eur. J. For. Path. 5 (1975) 129–137.
Bernier et al., "Induction and genetic characterization of . . . ", Mycol. Res. 98(8), 943–953 (1994).
Jeng et al., "A comparison of the nucleotide sequence of the . . . ", Curr Genet (1996) 29: 168–173.
Sutherland et al., "Control of Dutch elm disease by induced host resistance", Eur. J. For. Path. 25 (1995) 307–318.
Svircev et al., "Detection of Cerato–Ulmin on Aggressive Isolates . . . ", Phytopathology vol. 78, No. 3, 1988, pp. 322–327.
Hubbes et al., "Aggressiveness of Ceratocystis ulmi strains and . . . ", Eur. J. For. Path. 11 (1981) 257–264.
Yang et al., "A glycoprotein isolated from culture filtrates of . . . ", Mycol. Res. 98(3): 295–300 (1994).

*Primary Examiner*—Christopher S. F. Low
*Assistant Examiner*—David Lukton
*Attorney, Agent, or Firm*—Riches, McKenzie & Herbert

[57] ABSTRACT

A preventative treatment for wilt diseases in trees is disclosed which provides susceptible trees with induced resistance to wilt disease-causing organisms. The treatment comprises administering to a susceptible tree an amount of an elicitor effective to cause a defence reaction in the tree. The preferred elicitor for use as a treatment for Dutch elm disease and Fire Blight Disease is a novel elicitor isolated from cultures of *Ophiostoma ulmi*. The preferred elicitor is non-toxic and heat stable and is shown to be effective for inducing resistance to Dutch Elm Disease and Fire Blight Disease and in susceptible trees.

43 Claims, 8 Drawing Sheets

Experiment In Toronto
(4 weeks after challenging inoculation)

A  Elicitor treated on May 28, 1997; inoculated on
June 9, 1997 and evaluated on July 7, 1997

B  Wounded on May 28, 1997; inoculated on
June 9, 1997 and evaluated on July 7, 1997

Experiment in Toronto
(7.5 weeks after challenging inoculation)

A  Elicitor treated on May 28, 1997; inoculated on
June 9, 1997 and evaluated on July 31, 1997

B  Wounded on May 28, 1997; inoculated on
June 9, 1997 and evaluated on July 31, 1997

FIG. 4

```
              10         20         30         40         50         60
    GTGTCTTCTTCCTTCACCTCCGACAGCTCCATCGATGGCCTCGTCGGTCTGGGCTTCGAC
      V  S  S  S  F  T  S  D  S  S  I  D  G  L  V  G  L  G  F  D
       C  L  L  P  S  P  P  T  A  P  S  M  A  S  S  V  W  A  S
    T     V  F  F  L  H  L  R  Q  L  H  R  W  P  R  R  S  G  L  R 70         80         90        100        110        120
    AGCCTCAACTCCGCCTCCCCCAGCGCTGTTCCCACTTTCTTCGACAACATCATTGGTAGC
      S  L  N  S  A  S  P  S  A  V  P  T  F  F  D  N  I  I  G  S
        A  S  T  P  P  P  P  A  L  F  P  L  S  S  T  T  S  L  V  A
    Q  P  Q  L  R  L  P  Q  R  C  S  H  F  L  R  Q  H  H  W  -

130        140        150        160        170        180
    CTGGACAAGCCCGTTTTCACTGCTGATTTGAAGCACAACAAGGGTAAGTACTGCCTTTTC
      L  D  K  P  V  F  T  A  D  L  K  H  N  K  G  K  Y  C  L  F
        W  T  S  P  F  S  L  L  I  -  S  T  T  R  V  S  T  A  F  S
    P  G  Q  A  R  F  H  C  -  F  E  A  Q  Q  G  -  V  L  P  F 190        200        210        220        230        240
    TTGAACCTATCCACCAAAGAATAACCCATTAACTCCTCTTATTAGCCGGTTCATACGACT
      L  N  L  S  T  K  E  -  P  I  N  S  S  Y  -  P  V  H  T  T
        -  T  Y  P  P  K  N  N  P  L  T  P  L  I  S  R  F  I  R  L
    L  E  P  I  H  Q  R  I  T  H  -  L  L  L  A  G  S  Y  D 250        260        270        280        290        300
    TCGGTGTTATCGACAGCTCCAAGTACACCGGCGCCCTGACCTACGTTCCTGTTAACACCG
      S  V  L  S  T  A  P  S  T  P  A  P  -  P  T  F  L  L  T  P
        R  C  Y  R  Q  L  Q  V  H  R  R  P  D  L  R  S  C  -  H  R
    F  G  V  I  D  S  S  K  Y  T  G  A  L  T  Y  V  P  V  N  T 310        320        330        340        350        360
    ACCCCGGTTACTGGACATTCACCTCGTCTGGCTACGGAATTGGAACTGCTGCTTTCAAGT
      T  P  V  T  G  H  S  P  R  L  A  T  E  L  E  L  L  L  S  S
        P  R  L  L  D  I  H  L  V  W  L  R  N  W  N  C  C  F  Q  V
    D  P  G  Y  W  T  F  T  S  S  G  Y  G  I  G  T  A  A  F  K
```

FIG. 4 (CONTINUED)

```
              370         380         390         400         410         420
     CCACTAGCGTCACTGGTATTGCCGATACCGGTACTACCCTGCTGTACCTCGACACCGCCA

P  L  A  S  L  V  L  P  I  P  V  L  P  C  C  T  S  T  P  P
         H  -  R  H  W  Y  C  R  Y  R  Y  Y  P  A  V  P  R  H  R  H
       S  T  S  V  T  G  I  A  D  T  G  T  T  L  L  Y  L  D  T  A 430         440         450         460         470         480
     TCGTCAAGGCCTACTACGCACAGATCAGCGGTTCGTCCAACAGCGCTACTACGGTGGCTA

S  S  R  P  T  T  H  R  S  A  V  R  P  T  A  L  L  R  W  L
            R  Q  G  L  L  R  T  D  Q  R  F  V  Q  Q  R  Y  Y  G  G  Y
         I  V  K  A  Y  Y  A  Q  I  S  G  S  S  N  S  A  T  T  V  A 490         500         510         520         530         540
     CGTTTTCAAGTGCTCTGCCACCCCCCCTGATTTACTTCGGTGTCGGCAGTGCCACAATTA

R  F  Q  V  L  C  H  P  P  -  F  T  S  V  S  A  V  P  Q  L
            V  F  K  C  S  A  T  P  P  P  D  L  L  R  C  R  Q  C  H  N  Y
         T  F  S  S  A  L  P  P  P  L  I  Y  F  G  V  G  S  A  T  I 550         560         570         580         590         600
     CTATCCCCGGTAGCTACATTAACTACGGCCCCGTCACTCCGGCAGCACCACTTGCTTCGG

L  S  P  V  A  T  L  T  T  A  P  S  L  R  Q  H  H  L  L  R
            Y  P  R  -  L  H  -  L  R  P  R  H  S  G  S  T  T  C  F  G
         T  I  P  G  S  Y  I  N  Y  G  P  V  T  P  A  A  P  L  A  S 610         620         630         640         650         660
     CGGTCTGCAGGACAGCTCGGATATTGGCATCAACATCTTTGGCGATGTTGCCCTTAAGGC

R  S  A  G  Q  L  G  Y  W  H  Q  H  L  W  R  C  C  P  -  G
            G  L  Q  D  S  S  D  I  G  I  N  I  F  G  D  V  A  L  K  A
         A  V  C  R  T  A  R  I  L  A  S  T  S  L  A  M  L  P  L  R 670         680
     TGCGTTCGTTGTTTTCGACGGAAGGGC

```
              10         20         30         40         50         60
              |          |          |          |          |          |
       GGTTCCGCGGTGGCTACTCCATCCCTGTCAGATTGGTACCCCTGCCCAGGTTCTGAACTT
         G  S  A  V  A  T  P  S  L  S  D  W  Y  P  C  P  G  S  E  L
        V  P  R  W  L  L  H  P  C  Q  I  G  T  P  A  Q  V  L  N  L
          F  R  G  G  Y  S  I  P  V  R  L  V  P  L  P  R  F  -  T 70         80         90        100        110        120
              |          |          |          |          |          |
       GACTTGGACACTGGCTCGTCTGATCTATGGGTCTTCAGCAGCCTTACTCCTTCGTCTGAG
         D  L  D  T  G  S  S  D  L  W  V  F  S  S  L  T  P  S  S  E
        T  W  T  L  A  R  L  I  Y  G  S  S  A  A  L  L  L  R  L  R
       -  L  G  H  W  L  V  -  S  M  G  L  Q  Q  P  Y  S  F  V  -

130        140        150        160        170        180
              |          |          |          |          |          |
       GTCAATGGCCAATCGGTCTACACTCCTACGAAGAGCACCACCTCCAAGCTAGTCTCTGGC
         V  N  G  Q  S  V  Y  T  P  T  K  S  T  T  S  K  L  V  S  G
           S  M  A  N  R  S  T  L  L  R  R  A  P  P  P  S  -  S  L  A
        G  Q  W  P  I  G  L  H  S  Y  E  E  H  H  L  Q  A  S  L  W 190        200        210        220        230        240
              |          |          |          |          |          |
       GCCACCTGGCAGGTCTCCTATGGCGATGGCTCGTCGTCCAGTGGTGTCATCTACACTGAC
         A  T  W  Q  V  S  Y  G  D  G  S  S  S  S  G  V  I  Y  T  D
          P  P  G  R  S  P  M  A  M  A  R  R  P  V  V  S  S  T  L  T
        R  H  L  A  G  L  L  W  R  W  L  V  V  Q  W  C  H  L  H  -

250        260        270        280        290        300
              |          |          |          |          |          |
       AAGGTCACCATTGGCGGCATCACTGCTGCCAGCCAGGCTGTTGAGGCTGCCAAGGTTGTT
         K  V  T  I  G  G  I  T  A  A  S  Q  A  V  E  A  A  K  V  V
          R  S  P  L  A  A  S  L  L  P  A  R  L  L  R  L  P  R  L  F
        Q  G  H  H  W  R  H  H  C  C  Q  P  G  C  -  G  C  Q  G  C
```

FIGURE 5 (CONTINUED)

```
                670       680       690       700       710       720
                 |         |         |         |         |         |
         CTAGCGTCACTGGTATTGCCGATACCGGTACTACCCTGCTGTACCTCGACACCGCCATCG
          L  A  S  L  V  L  P  I  P  V  L  P  C  C  T  S  T  P  P  S
           -  R  H  W  Y  C  R  Y  R  Y  Y  P  A  V  P  R  H  R  H  R
             T  S  V  T  G  I  A  D  T  G  T  T  L  L  Y  L  D  T  A  I
             ─────────────────────────────────────────────────────────

730       740       750       760       770       780
                 |         |         |         |         |         |
         TCAAGGCCTACTACGCACAGATCAGCGGTTCGTCCAACAGCGCTACTACGGTGGCTACGT
            S  R  P  T  T  H  R  S  A  V  R  P  T  A  L  L  R  W  L  R
             Q  G  L  L  R  T  D  Q  R  F  V  Q  Q  R  Y  Y  G  G  Y  V
          V  K  A  Y  Y  A  Q  I  S  G  S  S  N  S  A  T  T  V  A  T
          ───────────────────────────────────────────────────────────

790       800       810       820       830       840
                 |         |         |         |         |         |
         TTTCAAGTGCTCTGCCACCCCCCCTGATTTACTTCGGTGTCGGCAGTGCCAGAATTACTA
           F  Q  V  L  C  H  P  P  -  F  T  S  V  S  A  V  P  E  L  L
            F  K  C  S  A  T  P  P  D  L  L  R  C  R  Q  C  Q  N  Y  Y
          F  S  S  A  L  P  P  P  L  I  Y  F  G  V  G  S  A  R  I  T
          ───────────────────────────────────────────────────────────

850       860       870       880       890       900
                 |         |         |         |         |         |
         TCCCCGGTAGCTACATTAACTACGGGCCCCGTCACTCCGGCAGCACCACTTGCTTCGGCG
           S  P  V  A  T  L  T  T  G  P  V  T  P  A  A  P  L  A  S  A
            P  R  -  L  H  -  L  R  A  P  S  L  R  Q  H  H  L  L  R  R
          I  P  G  S  Y  I  N  Y  G  P  R  H  S  G  S  T  T  C  F  G
          ───────────────────────────────────────────────────────────

910       920       930       940       950       960
                 |         |         |         |         |         |
         GTCTGCAGGACAGCTCGGATATTGGCATCAACATCTTTGGCGATGTTGCCCTTAAGGCTG
           V  C  R  T  A  R  I  L  A  S  T  S  L  A  M  L  P  L  R  L
            S  A  G  Q  L  G  Y  W  H  Q  H  L  W  R  C  C  P  -  G  C
          G  L  Q  D  S  S  D  I  G  I  N  I  F  G  D  V  A  L  K  A
          ───────────────────────────────────────────────────────────

970       980
                 |         |
         CGTTCGTTGTTTTCGACGGAAGGGC
            R  S  L  F  S  T  E  G
             V  R  C  F  R  R  K  G
          A  F  V  V  F  D  G  R
          ──────────────────────
```

FIGURE 5 (CONTINUED)

```
           310       320       330       340       350       360
            |         |         |         |         |         |
      TCTTCTTCCTTCACCTCCGACAGCTCCATCGATGGCCTCGTCGGTCTGGGCTTCGACAGC
       S  S  S  F  T  S  D  S  S  I  D  G  L  V  G  L  G  F  D  S
        L  L  P  S  P  P  T  A  P  S  M  A  S  S  V  W  A  S  T  A
      F  F  F  L  H  L  R  Q  L  H  R  W  P  R  R  S  G  L  R  Q 370       380       390       400       410       420
            |         |         |         |         |         |
      CTCAACTCCGCCTCCCCCAGCGCTGTTCCCACTTTCTTCGACAACATCATTGGTAGCCTG
       L  N  S  A  S  P  S  A  V  P  T  F  F  D  N  I  I  G  S  L
        S  T  P  P  P  P  A  L  F  P  L  S  S  T  T  S  L  V  A  W
      P  Q  L  R  L  P  Q  R  C  S  H  F  L  R  Q  H  H  W  -  P 430       440       450       460       470       480
            |         |         |         |         |         |
      GACAAGCCCGTTTTCACTGCTGATTTGAAGCACAACAAGGTAAGTACTGCCTTTTCTTG
       D  K  P  V  F  T  A  D  L  K  H  N  K  G  K  Y  C  L  F  L
        T  S  P  F  S  L  L  I  -  S  T  T  R  V  S  T  A  F  S  -
      G  Q  A  R  F  H  C  -  F  E  A  Q  Q  G  -  V  L  P  F  L 490       500       510       520       530       540
            |         |         |         |         |         |
      AACCTATCCACCAAAGAATAACCCATTAACTCCTCTTATTAGCCGGTTCATACGACTTCG
       N  L  S  T  K  E  -  P  I  N  S  S  Y  -  P  V  H  T  T  S
        T  Y  P  P  K  N  N  P  L  T  P  L  I  S  R  F  I  R  L  R
      E  P  I  H  Q  R  I  T  H  -  L  L  L  A  G  S  Y  D  F 550       560       570       580       590       600
            |         |         |         |         |         |
      GTGTTATCGACAGCTCCAAGTACACCGGCGCCCAGACCTACGTTCCTGTTAACACCGACC
       V  L  S  T  A  P  S  T  P  A  P  R  P  T  F  L  L  T  P  T
        C  Y  R  Q  L  Q  V  H  R  R  P  D  L  R  S  C  -  H  R  P
      G  V  I  D  S  S  K  Y  T  G  A  Q  T  Y  V  P  V  N  T  D 610       620       630       640       650       660
            |         |         |         |         |         |
      CCGGTTACTGGACATTCACCTCGTCTGGCTACGGAATTGGAACTGCTGCTTTCAAGTCCA
       P  V  T  G  H  S  P  R  L  A  T  E  L  E  L  L  L  S  S  P
        R  L  L  D  I  H  L  V  W  L  R  N  W  N  C  C  F  Q  V  H
      P  G  Y  W  T  F  T  S  S  G  Y  G  I  G  T  A  A  F  K  S
```

TREATMENT FOR WILT DISEASES OF TREES

CROSS-REFERENCE TO RELATED APPLICATIONS

This application is a continuation-in-part of U.S. parent application Ser. No. 09/048052, filed Mar. 26, 1998. this application claims the benefit of U.S. provisional patent application 60/041,630 filed Mar. 27, 1997.

FIELD OF THE INVENTION

This invention relates to treating wilt diseases of trees, by administering to trees an elicitor.

BACKGROUND OF THE INVENTION

Wilt diseases occur in various plants, notably woody perennial plants including trees. Wilt diseases involve the vascular system. An infected tree exhibits wilting symptoms with for example leaves, developing discoloration by reason of the disease interfering with water transport in the tree. The leaves typically eventually die and fall off. There is often discoloration or brown streaking in the vascular tissue. Diseased trees may soon die after the onset of the symptoms. Some examples of wilt diseases of trees included Dutch Elm Disease (DED), Fire Blight Disease(FBD), and diseases caused by Verticillium spp., Fusarium spp., and *Ceratocystis fagecearum* (Oak Wilt).

Since its introduction from Europe during the first half of the twentieth century, Dutch elm disease (DED) has decimated North American elm tree populations, the American elm (*Ulmus americana* L.) being particularly susceptible to DED.

DED is known to be caused by the fungus *Ophiostoma ulmi sensu lato* (*O. ulmi*), which is transported between elm trees by the native and European elm bark beetle. The beetle forms tunnels, also known as galleries, in the bark of the elm tree, and leaves spores of *O. ulmi* in these tunnels. The fungus then spreads through the tree's water-conducting tubes (vessels). The observable symptoms of DED, namely wilting, yellowing and loss of leaves, and eventually death, are believed to be caused by toxins released by the fungus. One such toxin, which has been associated with DED-like symptoms in American elms, is ceratoulmin (CU).

Fire Blight Disease (FBD) is an aggressive, devastating disease that infects several varieties of trees, including fruit trees, including apples and pears trees, as well as many members of the family Rosaceae. These include the following Genera and species varieties including Amelanchier (serviceberry), Exchorda (pearlbush),Potentilla (cinquefoil), Aroina (chokeberry), Fragaria (strawberry), Prinsepia, Aruncus (goatsbeard), Ceum (avnes), Prunus (apricot, cherry, plum), Chaenomeles (flowering quince), Heteromeles (toyon), Pyracantha (firethorn), Cotoneaster (cottoneaster), Holodiscus (creambush), Pyrus (pear), Cowania (cliff rose), Kageneckia, Raphiolepes (Indian hawthorn), Crataegomespilus, Kerria (Japanese rose), Rhodotypos (jetbead), Crataegus (hawthorn), Malus (apple, crabapple), Rosa (rose) Cydonia (quince), Mespilus (medlar), rubus (brambles), Dichotomanthes, Osteomeles, Sorbaria (false spirea), Docynia, Peraphyllum, Sorbus (mountain ash), Dryas (mountain avens), Photinia (photinia), Spiraea (spiraea), Eriobotrya (loquat), Physocarpus (ninebark) and Stranvaesia. While only affecting members of the rose family, the host range includes over 130 species and nearly 40 genera (Sinclair et al., Disease of Trees and Shrubs, Cornell University Press, 1987). FBD first appeared in the north eastern parts of North America approximately 200 years ago. It has since spread to New Zealand in 1916, England in 1957, Egypt in 1962 and various regions of Europe (Bereswill et al., App. Env. Micro. 58 (1992), pp. 3522–3526, van des Zwet and Bell, HortScience 30(6) (1995), pp. 1287–1291).

Caused by the gram negative bacterium *Erwinia amylovora* (*E. amylovora*), the principle symptoms of the disease consist of blackening of the succulent tissues on newly formed shoots, blight of blossoms and fruitlets as well as the formation of cankers that cause the twigs and branches to die back. In fact, the name is derived from the infected plant tissue appearing to be scorched by fire (Barny, Mol. Micro. 4(5) (1990), pp. 777–786). *E. amylovora* over winters at the margins of cankers from where it emerges by the formation of ooze with the onset of warm weather. Insects, rain splash, birds or humans are some of the vectors for the transmission of the pathogen. However, the most common vector are pollinators such as bees, flies and other insects. Infection courts are stigmas and nectarines, fresh wounds on any plant parts, stomata and lenticels on succulent twigs. It is from these places that the bacteria move rapidly into the vascular system of the host plant resulting in systemic infection and the symptoms associated with the disease (Sincliar et al., ibid.; Bellemann and Geider, J. General Microbiology 138 (1992), pp. 931–940; Momol et al., Plant Disease 82(6) (1998), pp. 646–650; and Bogs et al., Phytopathology 88(5) (1998), pp. 416–421).

As FBD and DED continues to spread and endanger valuable trees, numerous approaches have been tried over the years to eradicate or prevent the spread of DED and FBD in tree populations.

One approach to controlling DED has been to control elm bark beetle populations through the use of pesticides or by cutting infected limbs from elm trees. Another approach is to control or inhibit growth of the fungus by treating infected trees with fungicides or less commonly with antagonistic organisms such as bacteria. Several methods have also been employed to control FBD. One approach is to control the bacteria with antibiotic treatment. Unfortunately, *E. amylovora* is becoming progressively more resistant to antibiotic treatment with streptomycin (Lindow et al., Phytopathology 86(8) (1996), pp. 841–848; Loper et al., Plant Disease 75 (1991), pp. 287–290; and Moller et al., Plant Disease 65 (1981), pp. 563–568).

However, all of these approaches have disadvantages which limit their effectiveness. In particular, the use of large amounts of chemical pesticides and fungicides is undesirable from an environmental standpoint, particularly in urban areas. Unlike DED, controlling the insect vectors of the disease through the use of pesticides, is not a viable control method for FBD. This is because many of the insect vectors for FBD are the pollinators which are required for the production of fruit. Therefore, pest control of the insect vectors as a means for controlling FBD is not a possible avenue of prevention. In addition, the indiscriminate use of antibiotics to control FBD may have adverse health effects for humans.

Another approach has been to develop strains of elm trees which are resistant to DED, for example by selective breeding. However, such approaches are typically time consuming and do nothing to prevent the spread of DED in existing elm populations. Furthermore, until recently little was known about the mechanisms of DED resistance in elm trees or the means by which *O. ulmi* kills its host. Therefore, it was unclear whether or not long-term resistance could be bred into elm trees.

Furthermore, the importance of the American elm lies in its umbrella-shaped crown, which makes it a particularly effective shade tree. No other species of elm can compete with the American elm in this respect. Therefore, developing resistance by cross-breeding the American elm with resistant species of elms is useless if the form of the American elm is not maintained.

None of the above approaches has been completely successful in treating or controlling the spread of DED or FBD. Therefore, tree populations remain at risk of being decimated by DED and FBD.

The inventors appreciated that the American elm, which is particularly susceptible to DED, nevertheless produces a defence reaction when infected by a DED-causing fungus. Specifically, it has been shown that elm trees infected with DED produce several sesquiterpene quinones possessing antifungal properties, these compounds being known collectively as "mansonones", Dumas et al., Experiential 39 (1983), pp. 1089–1090. The mansonones known as mansonones "A", "C", "D", "E", "F" and "G" have all been shown to inhibit the growth of strains of *O. ulmi*. The structural formulas of these mansonones are shown below.

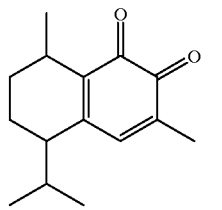

A

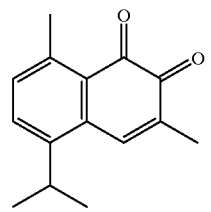

C

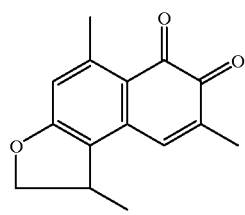

D

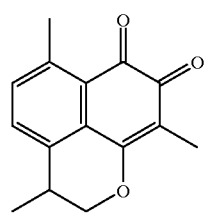

E

-continued

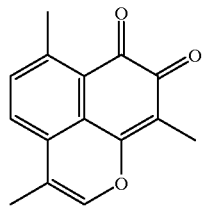

F

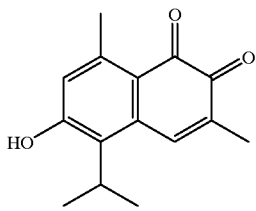

G

Mansonone accumulation in elms is believed to be triggered by specific compounds produced by *O. ulmi* which are recognized by the elm tree after it is infected by the fungus. Mansonone-inducing elicitors are present in the culture filtrate, cytoplasm and cell walls of *O. ulmi* and have been shown to induce production of mansonones in elm tissue cultures, Yang et al., Eur. J. For. Path. 23 (1993) 257–268, Can. J. Bot. 67 (1989) 3490–3497, and Mycol. Res. 98(3): 295–300 (1994).

Although all strains of *O. ulmi* produce elicitors, it has been found that the less virulent, "non-aggressive", strains of *O. ulmi* cause elm tissue to accumulate mansonones more quickly and in larger amounts than virulent, "aggressive", strains of *O. ulmi* (often referred to as *Ophiostoma novo-ulmi*). This is consistent with the observation that, although all strains can kill susceptible elm trees, the progress of the disease is slower in trees infected by non-aggressive isolates.

Several mechanisms have been proposed to explain the higher virulence of aggressive strains of *O. ulmi*. It is believed that differential elicitation and/or suppression of mansonone production in elms is at least partially responsible for the higher level of pathogenicity of aggressive strains of *O. ulmi*. Therefore, it appears that aggressive strains of the fungus may at least partially suppress the production of mansonones in elm trees.

Attempts have been made to use this difference in virulence to induce resistance to highly virulent strains of *O. ulmi* in susceptible elm trees. Some early inoculation trials using elm seedlings and elm tissue cultures were encouraging. For example, see, Hubbes and Jeng, Eur. J. For. Path. 11 (1981) 257–264, and Hubbes, Naturaliste can. (Rev. Ecol. Syst.), 115: 157–161 (1988). However, a more recent study conducted with European and hybrid elms concluded that, although there is some benefit to be derived from preventatively inoculating elms with *O. ulmi* or other fungi, there is little reason to think that the method has immediate promise for the control of DED, Sutherland et al., Eur. J. For. Path. 25 (1995) 307–318.

Therefore, extensive research has been conducted into the defence reactions of elms to DED-causing fungi. However, this research has thus far not resulted in any treatments for DED capable of being successfully used on a widespread basis.

The present inventor has appreciated that it may also be possible to induce a protective effect in trees against FBD through the use of the above-noted elicitor. This is a novel approach to control FBD as the DED elicitor is a non-toxic environmentally friendly substance that induces the FBD host's defense mechanism and thereby prevents the FBD pathogen from killing the host.

SUMMARY OF THE INVENTION

The inventor has overcome the problems in the prior art by inducing resistance to wilt diseases in plants by administering a glycoprotein in an amount sufficient to cause a defence reaction in the plant.

Wilt diseases to which the present invention relate involve the vascular system of the host plant and are expressed by wilting symptoms. Generally, the causal microorganisms of the wilting diseases grow in the vascular elements, cause discoloration of these elements and interference in water transport of the host plant. Some of the best known wilt diseases are found in woody perennial plants.

The invention is applicable to wilt diseases of plants with vascular systems, preferably woody perennial plants and more preferably trees, notably fruit trees and ornamental trees.

The invention is particularly applicable to all wilt diseases in trees and more particularly to Dutch elm Disease, Fire Blight Disease and diseases caused by Verticillum spp., Fusarium ssp., and *Ceratocystis fagecearum* (Oak Wilt). Insofar as the disease in Fire Blight Disease, the tree is preferably a Fire Blight Disease susceptible tree including fruit trees and trees selected from the family Rosaceae or from the groups of Malus or Pyrus.

An elicitor is a signalling agent that induce the expression of defence mechanisms in plants. The glycoproteins in accordance with the present invention preferably comprise glycoprotein elicitors which are administered in an amount sufficient to cause a defence reaction in a plant, preferably with the defence reaction comprising an accumulation of antimicrobial compounds in tissue of the plant. These elicitors can, for example, be products of microorganisms, plants or synthetic chemistry or molecular biology. In accordance with the present invention, the glycoprotein elicitor is preferably obtainable from a Dutch Elm Disease-causing fungus, with obtainable meaning either obtained from the fungus or being the same as that obtained from the fungus. the elicitor can be obtainable from the cell interior, cell wall or culture filtrate of a Dutch Elm disease-causing fungus, preferably *Ophiostoma ulmi,* more preferably a non-aggressive strain. The glycoproteins useful in accordance with the method of the present invention include those having an amino acid sequence which includes at least one fragment selected from sequences identified as obtainable from a non-aggressive strain of *Ophiostoma ulmi.*

More particularly, the inventor has overcome the problems in the prior art by inventing a treatment for DED which comprises a method for inducing resistance to DED in DED-susceptible elm trees and to FBD in FED susceptible trees. The treatment of the invention may be used preventatively to induce DED-resistance in uninfected elm trees or FED-resistance in uninfected trees, or may be used to treat elm trees which have been infected with a DED-causing fungus.

The method of the present invention in a preferred aspect comprises administering to a DED-susceptible elm tree, or a FBD-susceptible tree, an amount of an elicitor obtainable from a DED-causing fungus. Preferably, the method of the present invention utilizes a novel elicitor isolated from the culture filtrate of *O. ulmi* and having an amino acid sequence identified by the inventor.

The elicitors of the present invention, when administered to a DED-susceptible elm trees or FBD-susceptible trees, cause a defence reaction in the tree which inhibits the growth of DED-causing fungi or FBD causing bacteria. When used as a preventative treatment, the defence reaction allows the tree to resist subsequent infection by a DED-causing fungus such as *O. ulmi,* or FBD-causing bacteria such as *E. amylovora.* One of the most obvious responses making up this defence reaction in elm trees is the accumulation of mansonones by the tree.

Therefore, the DED treatment according to the invention mobilizes the elm tree's defence mechanism to protect it from present or future infection by a DED-causing fungus. Surprisingly, the DED treatment has also been found to provide protection against the FBD-causing bacteria. The present inventor appreciates that the method of the present invention has applicability to wilt diseases generally. The elicitors of the invention are non-toxic and stable and may easily be produced in large quantities from cultures of *O. ulmi.* Furthermore, only a small quantity of elicitor is required to trigger a defence reaction in a tree. The small quantities required may be easily administered without damaging the tree.

Therefore, the treatment according to the present invention provides significant advantages over known treatments, which typically require administration to the tree of large quantities of toxic materials either through a large number of holes in the tree or into the tree's root system.

Therefore, it is an object of the present invention to provide a treatment for plant wilt diseases, more preferably for wilt diseases of woody perennial plants.

It is another object of the present invention to provide a treatment for wilt diseases of woody perennial plants whether or not Dutch Elm Disease utilizing elicitors are obtainable from Dutch Elm Disease causing fungi.

It is another object of the present invention to provide a treatment for DED utilizing elicitors obtainable from DED-causing fungi.

It is another object of the present invention to provide a preventative treatment for DED utilizing elicitors obtainable from DED-causing fungi.

It is yet another object of the present invention to provide a treatment for DED utilizing a novel elicitor isolated from culture filtrates of *O. ulmi.*

It is yet another object of the present invention to provide a treatment for DED which utilizes the elm trees' natural defence reaction to DED-causing fungi.

It is yet another object of the present invention to provide a treatment for DED which causes the accumulation of fungistatic compounds such as mansonones in elm trees.

It is yet another object of the present invention to provide a treatment for FBD utilizing elicitors obtainable from DED-causing fungi.

It is yet another object of the present invention to provide a preventative treatment for FBD utilizing elicitors obtainable from DED-causing fungi.

It is yet another object of the present invention to provide a treatment for FBD utilizing a novel elicitor isolated from culture filtrates of *O. ulmi.*

It is yet another object of the present invention to provide a treatment for FBD which causes the accumulation of antibacterial compounds in trees.

Accordingly, in one aspect the present invention provides a method for inducing resistance to a wilt disease in a plant, preferably a woody perennial plant and more preferably a tree, comprising administering a glycoprotein in an amount sufficient to cause a defense reaction in the plant. Preferably, the glycoprotein is obtainable from a Dutch Elm Disease causing fungus, and the defense reaction comprises accumulation of growth inhibitory compounds in tissue in the plant. In another aspect, the glycoprotein comprises a glycoprotein having an amino acid sequence which includes at least one fragment selected from the group comprising SEQ.ID NO. 1, SEQ. ID NO. 2, SEQ. ID NO. 3, SEQ. ID NO.4, SEQ. ID NO. 15 and SEQ. ID NO. 16 as discussed hereinafter.

In another aspect, the present invention provides a method for inducing resistance to Dutch Elm Disease in a DED-susceptible elm tree, comprising administering to the tree a glycoprotein elicitor in an amount sufficient to cause a defence reaction in the tree. The defence reaction comprises accumulation of inhibitory compounds to fungal growth in tissue of the tree, and the elicitor is obtainable from a DED-causing fungus.

Another aspect of the present invention provides a method for inducing resistance to FBD in a FBD-susceptible tree, comprising administering to the tree a glycoprotein elicitor in an amount sufficient to cause a defence reaction in the tree. The defence reaction comprises accumulation of bacterial growth inhibitory compounds in tissue of the tree, and the elicitor is obtainable from a DED-causing fungus.

Preferably, the elicitor is obtainable from the cell interior, cell wall or culture filtrate of a DED-causing fungus, the preferred DED-causing fungus being *Ophiostoma ulmi* (*O. ulmi*), most preferably a non-aggressive strain of *O. ulmi*.

The elicitor is preferably a glycoprotein obtained from a culture filtrate of *O. ulmi* strain Q412, and having an amino acid sequence which includes SEQ. ID NO. 1, described hereinafter, which preferably begins at the N-terminal of the amino acid sequence of the elicitor. The molecular weight of the elicitor is preferably at least about 21 kDa.

Preferably, when used against DED in elm trees, the fungal inhibitory compounds accumulated by the elm tree are mansonones selected from the group comprising mansonones A, C, D, E, F and G. Although the defence reaction comprises accumulation of similar such mansonones, whether in elm trees or otherwise, it also preferably comprises lignification and release of hydrogen peroxide.

Preferred DED-susceptible elm trees to be treated according to the present invention are selected from the group comprising *Ulmus americana* L., *Ulmus thomassii* Sarg., *Ulmus rubra* Muhl., *Ulmus carpinifolia* Gleditsch., *Ulmus glabra* Huds., *Ulmus procera* Salisb. and *Ulmus laevis* Pall., and DED-susceptible cultivars thereof. The most preferred DED-susceptible elm tree is *Ulmus americana* L.

Surprisingly, the glycoprotein elicitor in accordance with this invention obtainable from DED-causing fungus has been found to be effective to treat wilt diseases other than DED. In particular, the inventor has found such elicitors as effective against FBD. Preferred FBD-susceptible trees to be treated according to the present invention are selected from the group comprising genus Malus and Pyrus. The most preferred FBD-susceptible trees are varities of pear and apple trees.

The dosage form and methods of application of the elicitor are generally the same for trees whether elm trees for the treatment of DED or other trees for treatment of FBD.

The amount of elicitor effective to cause the tree to exhibit a defence reaction is preferably from about 0.1 mg to about 150 mg. In one preferred aspect of the present invention, administering of the elicitor to the tree comprises injection of a liquid composition containing the elicitor into the tree, the liquid composition preferably comprising an aqueous solution of the elicitor in a preferred concentration of from about 0.1 mg/mL to about 50 mg/mL. Preferably, the injection delivers the liquid composition inside the vascular system adjacent to the bark of the tree.

In another preferred aspect of the invention, administering of the elicitor to the tree comprises insertion of the elicitor in a solid form into the tree, the solid form of the elicitor preferably comprising a solid composition comprising the elicitor, and which is preferably contained in a capsule. The solid composition may preferably additionally comprise acceptable fillers and carriers. Insertion of the elicitor into the tree preferably comprises drilling a hole through the bark of the tree, and inserting the capsule into the hole so that the elicitor is received inside the vascular system adjacent to the bark of the tree.

In another aspect, the present invention provides a program for prevention of wilt diseases in a tree, Dutch Elm Disease in a DED-susceptible elm tree, or Fire Blight Disease in a FBD-susceptible tree comprising annual treatment of the tree according to the method of the invention.

BRIEF DESCRIPTION OF THE DRAWINGS

Further aspects and advantages of the present invention will become apparent from the following description, taken together with the accompanying drawings, in which:

FIG. 4 which is on two drawing sheets, shows SEQ. ID NOS. 3, 4 and 5, along with possible amino acids located between SEQ. ID NOS. 3 and 4.

FIG. 5 which is on three drawing sheets, shows SEQ. ID NOS. 3, 4, 5, 9, 13, 15 and 16 along with possible amino acids located before SEQ. ID NO. 3 and between SEQ. ID NOS. 3 and 4.

DETAILED DESCRIPTION OF PREFERRED EMBODIMENTS

Figure 1:
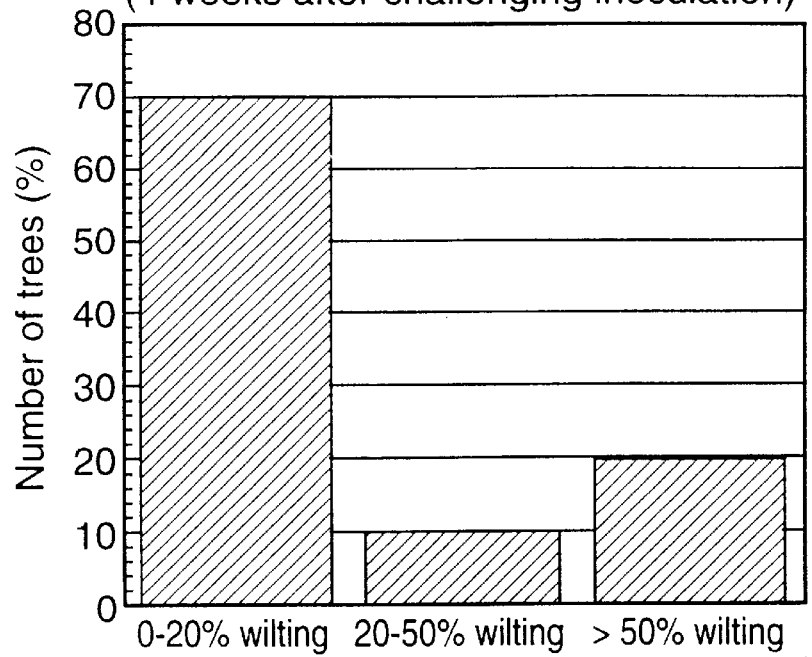
FIGS. 1A–1B provide a graphic illustration of test results obtained in DED tests conducted in Toronto four weeks after challenging inoculation.
Figure 1:
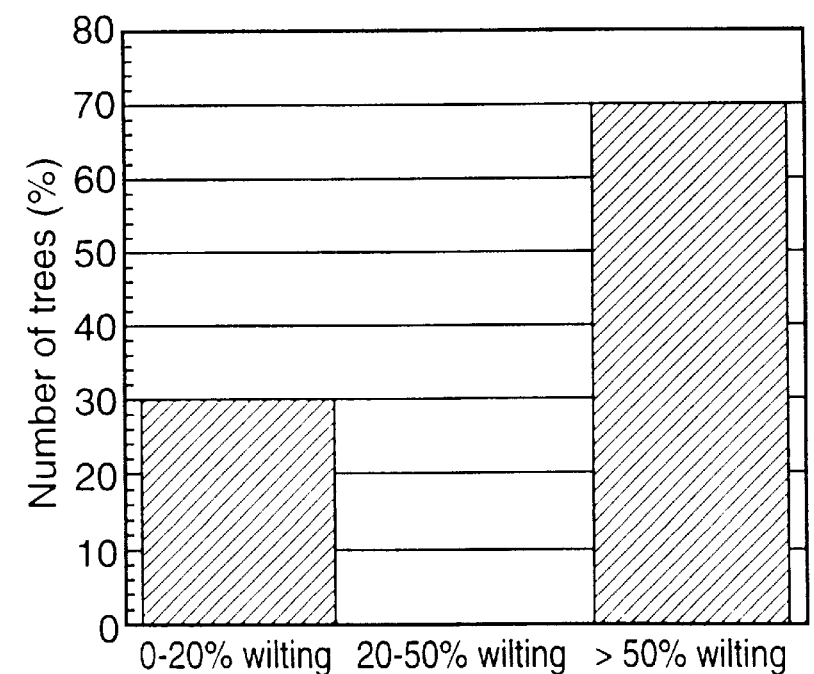

Elicitors according to the present invention are obtainable from DED-causing fungi. Preferably, the elicitors are isolated from culture filtrates, from cell walls, or from inside the cells of a DED-causing fungus.

More preferably, elicitors are isolated from culture filtrates of *O. ulmi*. Most preferably, elicitors according to the present invention are isolated from culture filtrates of non-aggressive strains of *O. ulmi*, such as strain Q412.

The inventor has isolated from the culture filtrate of strain n Q412 an elicitor comprising a glycoprotein having a molecular weight of at least about 21 kDa and containing the amino acid sequence presented below and in Sequence ID No. 1, beginning from the N-terminal:

```
Ala Glu Pro Val Phe Ala Val Ser Asn Phe
1               5                   10
Gln Ala Gly Cys Ile Pro His Xaa Ser Gln
                15              20
Gln Arg Xaa Tyr Phe Asp Xaa Val Lys Xaa
                25                  30
Xaa Xaa Gly
``` wherein
  Xaa at res. 18=(His or Ser);
  Xaa at res. 23=(Tyr or Arg);
  Xaa at res 27=(Asp or Val);
  Xaa at res 30=(Thr or Lys);
  Xaa at res 31=(Lys, Gly or Thr); and
  Xaa at res 32=(Thr or Gly).

The following additional N-terminal fragment of the above elictor, identified herein as SEQ. ID NO. 2, has been identified by the inventor:

```
Leu Val Ser Gly Ala Thr Trp Gln Val Ser
                5                   10
Tyr Gly Asp Gly Arg Tyr Xaa Ile Gln Val
                15                  20
Ile Xaa Xaa
``` wherein
  Xaa at res 17=(Ala or Val);
  Xaa at res 22=(Tyr or Ile); and
  Xaa at res 23=(Ala or Pro).

The methods of identification used by the inventor to identify amino acid sequences of the glycoprotein elictior and the DNA sequences of its corresponding gene are conventional molecular biology methods known to person skilled in the art. For example, Example 8 has been included describing the materials and methods for the preparation and sequencing of the DNA sequences corresponding to portions of the glycoprotein elicitor gene shown in SEQ. ID NOS. 5, 9 and 13.

The disclosure refers to and includes amino acid and DNA sequences identified herein as SEQ. ID NO. 1 to SEQ. ID NO. 16 and which sequence listings are provided on an appendix Sequencing Listing having ten pages.

FIG. 4 shows SEQ.ID NO. 5 as comprising a DNA sequence consisting of an upper line of numbered nucleotide base pairs 1 to 687. Three different possible amino acids sequences, corresponding to SEQ. ID NO. 5, are shown in the standard one letter code for each amino acid, below the DNA sequence. The amino acid sequence corresponding to amino acid SEQ. NO. 3 and SEQ NO. 4 are each underlined on FIG. 4.

FIG. 5 shows SEQ. ID NO. 9 and SEQ. ID NO. 13 as comprising a DNA sequence consisting of an upper line of numbered nucleotide base pairs 1 to 985. Three different possible amino acid sequences, corresponding to SEQ. ID NOS.5 and 9, are shown in the standard one letter code for each amino acid, below the DNA sequence. Each amino acid sequence underlined with a single line is a portion of the expected amino acid sequence of the glycoprotein elicitor. A portion of the DNA sequence which is believed to correspond to an intron is represented by nucleotides 461 to 603 and is underlined with a double line. The splicing of this intron is believe to result in a reading frame shift for the corresponding amino acid sequences that follow the intron. SEQ. ID NO. 15 and SEQ ID NO. 16 are the amino acid sequence underlined on FIG. 5 on either side of the intron. SEQ. ID NO. 14 corresponds to SEQ ID NO. 15 and SEQ ID NO. 16 combined. Each of SEQ. ID NO. 6 and SEQ ID NO. 10 comprises SEQ. ID NO. 3 and SEQ. ID NO. 4 combined. Each of SEQ ID NO. 7 and SEQ ID NO. 11 corresponds to SEQ. ID NO. 3. Each of SEQ. ID NO. 8 and SEQ. ID NO. 12 corresponds to SEQ. ID NO. 4.

The inventor has appreciated that as the elicitor obtainable from a DED causing fungus, a glycoprotein having an amino acid sequence which includes at least one fragment selected from the group comprising SEQ. ID NOS. 1, 2, 3, 4, 15 or 16 would produce the desired result.

A glycoprotein having amino acid sequences which includes at least one fragment selected from group comprising SEQ. ID NOS. 1, 2, 3, 4, 15 or 16 could be produced by one of several known methods including, but not limited to, recombinant DNA technology or protein synthesis.

Efforts to isolate the elicitor gene led to the identification of amino acid SEQ. ID NOS. 3 and 4 and DNA SEQ. ID NOS. 5 and 9. There is believed to be a gap of about 200 base pairs between the portion of the gene encoding the N-terminal of the amino acid sequence, at which SEQ. ID NOS. 1 and 2 have been identified, and the portion of the gene having DNA SEQ. ID NO. 5. SEQ. ID NOS. 9 and 13 disclose an additional 297 base pairs 5' to the DNA sequence disclosed in SEQ. ID NO. 5.

While the N-terminal sequences do not show any homology to any published protein, the identification of SEQ. ID NOS. 3, 4 and 5 allowed the inventor to determine the nature of the elicitor. SEQ. ID NOS. 3, 4, 5 and 9 are also shown in FIGS. 4 and 5, which also identifies the possible amino acids before SEQ. ID NO. 3 and between SEQ. ID NOS. 3 and 4. Based on homology comparisons with sequences published in a gene bank, the inventor found that the elicitor shows the greatest homology to asparatic proteinases from fungi such as *Glomerella cingulata* (65.6% homology), *Podospora anserian* (62.6% homology), *Rhizopus chinensis* (51.8% homology) and *Cryphonectria* (Endothia) *parasitica* (62.6% homology).

In general, asparatic proteinases are a group of proteinases that possess two catalytic aparatyl residues and have a variety of important biological functions such as programmed cell death (apoptosis). Although asparatic proteinases are widely dispersed in the animal and plant kingdom, and have been isolated from bacteria and the HIV virus, only relatively few are glycoproteins. Furthermore, although some of the asparatic proteinases have been linked to virulence factors of its producer, none have been shown to induce resistance in its host.

Although the fragments of the elicitor comprising SEQ. ID NOS. 1 to 4, 15 or 16 form part of an amino acid sequence of an elicitor obtained from strain Q412, it is believed by the inventor that elicitors obtained from cells or cell walls of DED-causing fungi, or obtained from strains of *O. ulmi* other than Q412, would have amino acid sequences having a high degree of homology to the amino acid sequence for the Q412 culture filtrate elicitor. Therefore, the present invention includes within its scope all elicitors obtainable from DED-causing fungi, and fragments and variants thereof, which cause a defence reaction in wilt disease susceptible plants, such as DED-susceptible elm trees, comprising the accumulation of fungal inhibitory compounds in such plants.

In a particularly preferred method for producing culture filtrate elicitors according to the present invention, a culture of *O. ulmi* is initiated from a mycelia plug and incubated for about 10 days on a culture medium, for example Wilson's medium. After incubation, the spores and mycelium are removed by centrifugation and the polysaccharides are removed by precipitation and filtering of the medium. The medium is then passed through a PM10 ultrafilter to produce a concentrated protein fraction containing at least one elicitor, which is then lyophilized (freeze dried).

It is to be appreciated that elicitors according to the invention may be produced on a large scale from cultures of DED-causing fungi, preferably *O. ulmi*, incubated in a fermenter.

It is to be further appreciated that elicitors according to the present invention do not need to be purified before being used. Rather, the elicitors may be used in crude or partially purified form.

Elicitors according to the invention are non-toxic, heat stable, and may be stored in powder form indefinitely without adverse consequences. The stability of the elicitors allows them to be administered to trees in a variety of forms. Preferably, elicitors are administered in solid form or liquid form. Preferred solid forms include tablets and capsules, and preferred liquid forms include injectable compositions.

Surprisingly, the glycoprotein elicitor developed initially in accordance with the present invention from DED-causing fungus for the treatment of DED has been found to be effective to treat wilt diseases other than DED, and particularly to treat FBD. The dosage, form, method of application and delivery of the elicitor for treatment of FBD in FBD susceptible trees is substantially the same for treatment of DED in elm trees. In the following discussion, the reference to trees or elm trees or treatment of DED in elms is equally applicable to trees for treatment of other wilt diseases notably FBD and to FBD susceptible trees.

Regarding DED, the elicitors according to the present invention are administered to an elm tree in an amount sufficient to produce a defence reaction in the tree, in which sufficient fungal inhibitory compounds such as mansonones are accumulated to provide the tree with induced resistance to Dutch elm disease.

Similarly, regarding FBD, the elicitors according to the present invention are administered to trees in an amount sufficient to produce a defence reaction in the tree, in which sufficient anti-bacterial activity is elicited to provide the tree with induced resistance to FBD.

The preferred dose of elicitor depends on a variety of factors, including the time of the year, size and vigor of the tree. However, the inventor has observed that small doses of elicitor may be as effective as larger doses to induce resistance in trees.

For example, the inventor has found that for trees having diameters (measured about the trunk) ranging from about 20 cm to greater than 100 cm, doses of at least about 5 mg of elicitor are preferred. More preferably, the amount of elicitor administered is from about 5 mg to about 150 mg, and most preferably from about 10 mg to about 80 mg. Ranges of the elicitor of about 0.1 mg to about 150 mg can be effective under some circumstance.

When administered in solid form, elicitors are preferably incorporated into a capsule which can be dissolved by the tree. Other ingredients, such as fillers and carriers, may also be added to the capsule as required. The capsule is preferably administered by drilling a small hole into the tree, preferably on its trunk or stem, and then inserting the capsule into the hole so that it becomes received inside the outer sapwood and bark of the tree. The elicitor can also be applied as a paste applied to pruning wounds during the tree pruning season.

When administered in liquid form, elicitors can be either injected into the stems or applied as a spray during the flowering period since it is harmless to the pollinating insects. When elicitors are to be injected, they are preferably incorporated into an injectable composition which is injected through a small pre-drilled hole into the tree, preferably into the trunk, and preferably inside the bark into the outer vascular system.

Preferably, the injectable composition comprises an aqueous solution of elicitors. The composition may comprise additional ingredients, such as carriers and cosolvents, as required.

More preferably, the injectable composition comprises an aqueous solution containing the above preferred elicitor at concentrations ranging from about 0.1 to about 50 mg/mL. Other preferred ranges include preferably from about 0.5 to about 2 mg/mL and from 10 to about 50 mg/mL. The volume of composition injected is preferably from about 5 mL to about 100 mL with other ranges of from about 20 mL to about 100 mL, about 10 mL to about 50 mL, and preferably from about 20 mL to about 40 mL.

The elm trees to which the elicitors according to the invention are administered are those which are susceptible to DED. Preferred elms to which the elicitors are administered are DED-susceptible European and North American varieties of elm and hybrids and cultivars thereof, which range from being moderately to very susceptible. Preferred North American elms include *Ulmus americana* L., *Ulmus thomassii* Sarg. and *Ulmus rubra* Muhl., and their susceptible cultivars. Preferred European elms include *Ulmus carpinifolia* Gleditsch., *Ulmus glabra* Huds., *Ulmus procera* Salisb. and *Ulmus laevis* Pall., and their susceptible cultivars. Most preferably, elicitors according to the invention are administered to the American elm (*Ulmus americana*), which is a particularly desirable elm species and is highly susceptible to DED.

The administration of elicitors according to the invention to a susceptible elm tree causes a defence reaction to occur in the tree. It is known that this defence reaction includes the accumulation in the tree of mansonones, which as described above are sesquiterpene quinones having antifungal activity.

However, the inventor has found that administration of elicitors according to the invention to elm trees or other trees causes a cascade of events which together comprise the tree's defence reaction. Specifically, the inventor has found that administration of elicitors to susceptible trees and particularly elm trees also results in lignification of tissues exposed to the elicitors. Lignification is believed to prevent or slow the spread of fungus in a tree. The inventor has also found that susceptible elms treated with elicitors produce hydrogen peroxide ($H_2O_2$), which is believed to trigger lignification. It has also been found by the inventor that administration of elicitors to elms triggers the accumulation of fungal inhibitory compounds other than mansonones.

The inventor has further found that it is preferred to administer elicitors to susceptible elms annually in order to provide adequate protection from DED. Annual treatment is preferred so that the defence reaction triggered by the elicitor may occur in each newly formed annual tissue (ring). Although at least partially dependent on climate, elicitors may be administered to elm trees at any time of year, preferably before beetles which transmit the DED fungus become active. Therefore, elm trees are preferably treated with elicitors in spring. Similarly, other trees and plants to be treated for protection from other wilt diseases may be treated at suitable times annually.

The elicitors of the invention may be used to treat DED-infected trees or may be used preventatively to induce resistance in healthy trees. When used to treat infected trees, the elicitors induce resistance to DED in parts of the tree which have not been infected, thereby preventing spread of the fungus to healthy parts of the tree. Preferably, dead or infected branches are cut off to further prevent spread of the fungus.

EXAMPLES

1. Preparation of Elicitor

An elicitor having the above-described amino acid sequence was isolated from a 10 day old culture of Q412, a non-aggressive isolate of *O. ulmi*. The culture was initiated from a mycelia plug maintained in 10% glycerol at −70° C. The culture media were prepared in 4 L quantities in 15 L Nalgene fermenter flasks and autoclaved at 121° C. for 30 minutes. The fermenter flasks were inoculated with 25 mL of a turbid spore suspension from a 3 day old culture. The flasks were incubated at 25° C. with shaking at 125 rpm for 10 days. The spores were removed by centrifugation and the polysaccharides precipitated with an equal volume of ethanol. The precipitated culture broth was filtered through a Whatman #42 filter and the ethanol removed on a Buchi rotovapor under reduced pressure. The water component was subsequently filtered through a 0.22 μm filter. The protein component was concentrated on a PM10 filter and lyophilized. The composition of the lyophilized product was analyzed by gel electrophoresis to verify the presence of the elicitor.

2. Preparation of Elicitor Compositions

Injectable elicitor compositions were prepared by dissolving the lyophilized elicitor obtained in Example 1 in distilled water. Three different compositions of varying concentration were formed, namely 0.5 mg/mL, 1 mg/mL, and 2 mg/mL.

3. Administration of Elicitor Compositions to Elm Trees

The experimental site was located north of Sault Ste. Marie, Ontario, in Tilley township. Elm saplings free from DED, and ranging in diameter from 21 to 72 cm, were divided into three diameter classes: 20 to 30 cm (8 trees), 31 to 49 cm (24 trees), and 50 cm or greater (12 trees). All eight trees in the 20 to 30 cm diameter class were injected, with each of the above concentrations of elicitor being injected into two trees, and two trees being injected with distilled water (control). All 24 trees in the 31 to 49 cm diameter class were injected, each concentration of elicitor being injected into six trees, and six trees being injected with distilled water (control). All twelve trees in the 50 cm or greater diameter range were injected, each concentration of elicitor being injected into three trees, and three trees being injected with distilled water (control). However, one particularly large tree, having a diameter of greater than 100 cm, was treated with 80 mg of elicitor (2 mg/mL×4 mL) due to its size. All trees except this tree received two injections from a maujet injector, each injection having a volume of 10 mL. The tree having a diameter greater than 100 cm was received four injections from a maujet injector. All injections were carried out on Jun. 12, 1996.

Ten days later, 1 tree from each diameter class which had been injected with 2 mg/mL elicitor was sacrificed and extracted for mansonones according to the procedure described in Dumas et al., Experientia 39 (1983), pp. 1089–1090. Although mansonones were undetectable visually by thin layer chromatography (TLC), once the plates were sprayed with *Cladosporium cucumerinum,* the presence of mansonone C and the large inhibitory tailing type fraction characteristic of mansonones were evident.

4. Challenge Tests With DED Fungus

On Jun. 26, 1996, all trees which were injected as in Example 3 above were challenged with an aggressive isolate of *O. ulmi* (CESS 16K), with the exception of four trees in the 31 to 49 cm diameter class. These four trees, respectively injected with 0.5 mg/mL, 1 mg/mL and 2 mg/mL elicitor and the distilled water control, were not challenged to see whether the elicitor alone would cause any symptoms. The amount of CESS 16K injected into each tree was 1 mL at a concentration of $1\times10^4$ spores/mL.

5. Observations and Conclusions

The site was visited during the second week of July, 1996. The four saplings in the 31 to 49 cm diameter class which were treated only with elicitor or the control did not display any phytotoxic symptoms throughout the period. Dormancy initiation was normal and did not differ from untreated elms.

The trees which were challenged with *O. ulmi* as described in Example 4 above showed the typical symptoms of DED, namely yellowing of leaves, drooping of branches, loss of leaves, etc., and appeared to be dead.

On Sep. 5, 1996, it was observed that trees which had been treated with the distilled water control and subsequently challenged with *O. ulmi* were dead. On the other hand, only one of the 33 trees which had been treated with elicitor before being challenged with *O. ulmi* was dead. The dead tree was the large elm mentioned above having a diameter of greater than 100 cm, which had been injected with 80 mg of elicitor. It may be that this particularly large tree required even more elicitor. The other trees which had been treated with elicitor before challenge with *O. ulmi* were showing signs of life. For example, it was observed that the bark on the stem (trunk) and the branch tips was green and new foliage, although smaller than the foliage lost by the tree, had formed. In the surviving trees, there were no apparent differences caused by the differing concentrations of elicitor injected. CESS 16K was re-isolated from a subset of the challenged elms, and therefore it was concluded that the pathogen did in fact infect the trees.

The trees were left standing and the site was revisited on Dec. 10, 1996 to collect branches in order to determine if bud break would occur. It was observed that most of the trees treated with elicitor and challenged with *O. ulmi* had died, with the exception of two trees. However, examination of the branches showed that the deaths of the trees were caused by the inability of the trees to initiate new buds for the following spring. It is believed that this was due to the late period at which the inoculations were carried out, the trees not having enough time to form new buds. The first frost, which is experienced in early autumn at the test site, most likely killed the trees.

Therefore, although most of the treated trees eventually died, it is predicted that inoculation of trees earlier in the spring at this test site, for example as soon as the leaves reached their full size, would have resulted in most or all of the trees surviving the winter. Furthermore, had the tests been conducted on elm trees in a warmer climate, it could reasonably be predicted that most, if not all, of the trees would have survived the inoculations.

6. Additional Tests

In 1997, additional tests on induced resistance were carried out in Toronto and Sault Ste. Marie, Ontario, Canada.

On May 28, 1997, 40 five year old elm saplings grown at the University of Toronto Faculty of Forestry's nursery located at Mississauga near Toronto were treated with the elicitor. To facilitate the elicitor treatment, the elicitor was administered in the form of a 1.5×10 mm capsule.

Capsules were prepared by mixing a 10 mg/ml solution of elicitor with 0.5% gelatin and filling 1 ml containers with the resulting mixture. The filled containers were first placed in a deep freezer at −20° C. and, after freezing, were transferred to a freeze dryer. After freeze drying, the 1 ml capsules became very flexible and could easily be rolled into 1.5×10 mm treatment plugs.

Four holes of 1.5 mm diameter and 10 mm depth were drilled into the stem of each sapling, about 5 cm above ground level, with a portable electric drill. One capsule was inserted into each bore hole. The bore holes were then closed with parafilm. Controls (9 saplings) received only gelatin capsules without elicitor.

On Jun. 9, 1997, 2 bore holes were drilled in each tree. Into each bore hole about 1.5 million spores of an aggressive strain of the DED fungus were injected by syringe. After injecting the DED fungus, the holes were closed with parafilm.

Figure 2:
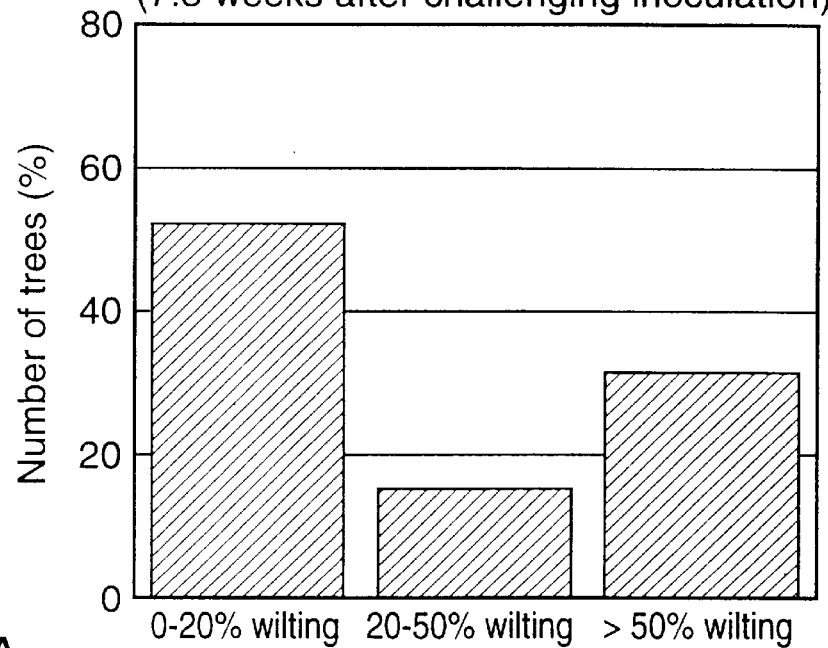
FIGS. 2A–2B provide a graphic illustration of test results obtained in DED tests conducted in Toronto 7.5 weeks after challenging inoculation.
Figure 2:
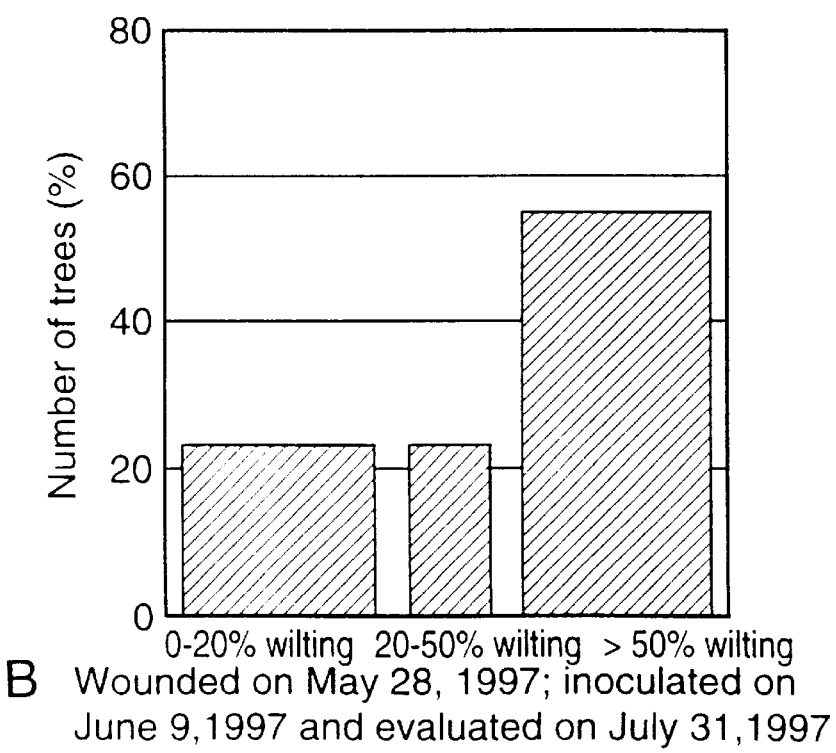

Treated and control trees were evaluated for wilting of leaves on Jul. 7, 1997, 4 weeks after the challenging inoculation, and on Jul. 31, 1997, 7.5 weeks after the challenging inoculation. The results are shown in FIGS. 1 and 2. Trees were classified according to their leaf symptoms (degree of wilting) in three categories, 0–20%, 20–50% and 50–100%. Statistical analysis showed that the trees treated with elicitor showed significantly less wilting than the control trees.

Figure 3:
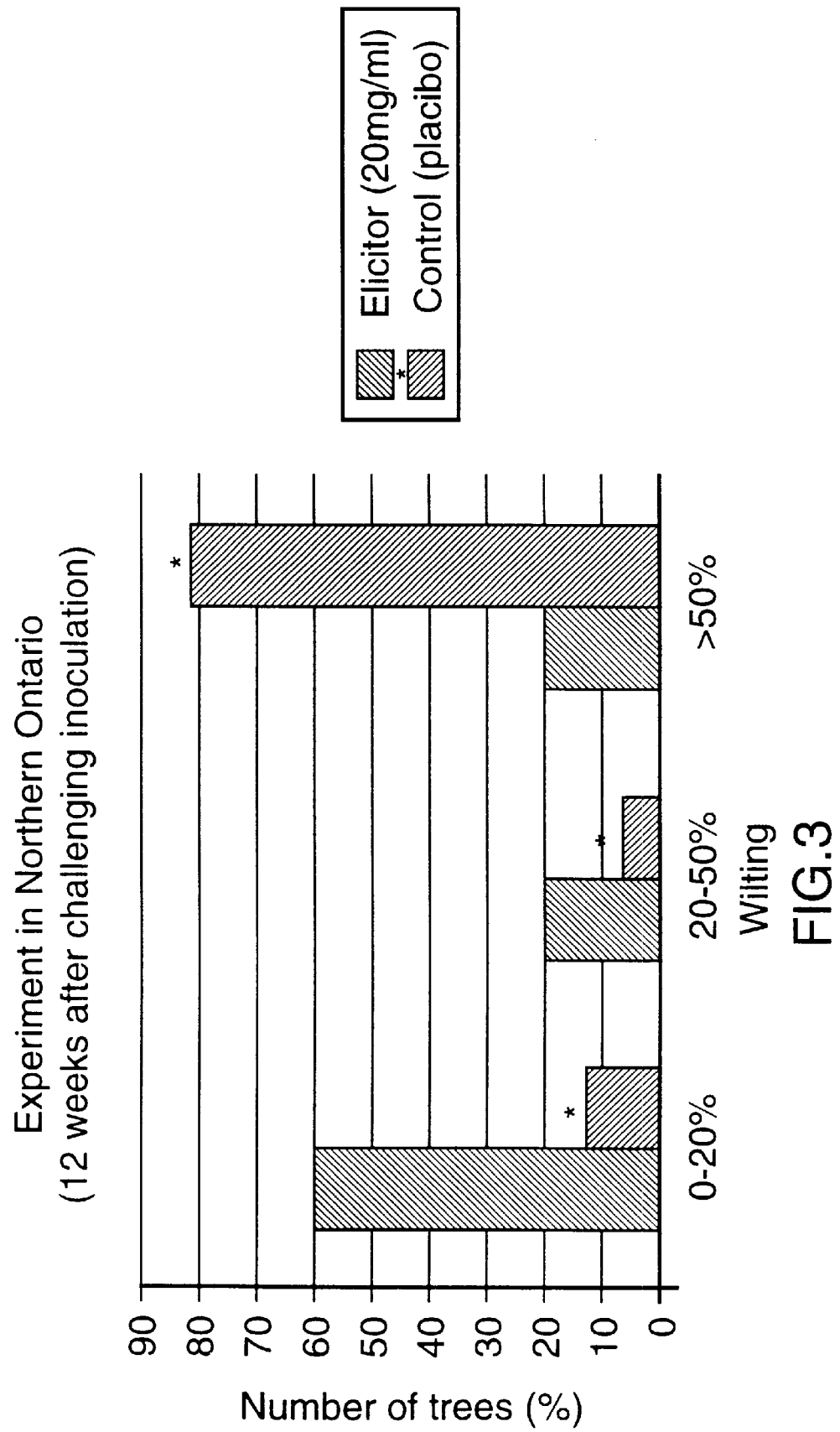
FIG. 3 is a graphic illustration of DED test results obtained in tests conducted in Northern Ontario (Sault Ste. Marie) twelve weeks after challenging inoculation.

On Jun. 11, 1997, 25 trees in Sault Ste. Marie were treated as described above in the Toronto tests with the exception that the elicitor capsules were prepared from a 20 mg/ml solution of elicitor. The diameter at breast height (DBH) of the trees varied from between 35 and 90 mm. All trees were challenged by inoculation with 8,000 spores of an aggressive strain of DED fungus on Jun. 27, 1997. Symptom evaluation was carried out twelve weeks after inoculation. The results are shown in FIG. 3. As in the Toronto tests, a significant difference was observed between the trees treated with elicitor and the control trees.

7. Challenge Test with FBD bacteria

35 Golden Delicious seedlings were grown in a greenhouse to a height of about 60 cm in single pots. 20 seedlings were randomly chosen and wounded as the control group, while 15 seedlings were treated with the 20 μl of the elicitor at a concentration of 20 mg/ml as the treated group. One week after the treatment, 10 seedlings from the control group (group 2) and 10 seedlings from the treated group (group 3) were challenged with the virulent *E. amylovora* strain *E.a.* 6-4 at a concentration of $10^8$ CFU/ml by injection into the seedling. The remaining 5 seedlings from the treated group (group 4) were challenged 14 days later. The time delay for group 4 was to determine whether the time between elicitor treatment and pathogen challenge leads to higher host resistance. Group 1, consisted of the remaining 5 seedlings from the control group that was not infected with the virulent pathogen. The level of infection are set forth below in Table 1:

TABLE 1

| Group | Number and Degree of Infection | | | | | |
|---|---|---|---|---|---|---|
| | 0 | 1 | 2 | 3 | 4 | 5 |
| Group 1; No infection, no treatment | 10 | 0 | 0 | 0 | 0 | 0 |
| Group 2; No treatment, infected | 0 | 0 | 0 | 2 | 8 | 0 |
| Group 3; Elicitor treated, infected after 7 days | 5 | 3 | 0 | 2 | 0 | 0 |
| Group 4; Elicitor treated, infected after 14 days | 4 | 1 | 0 | 0 | 0 | 0 |

Each of the four groups were evaluated on symptom formation according to a 0–5 scale, where 0 is no symptom and 5 dry dark brown dead leaves. In group 3, none of the infected seedlings demonstrated any wilting, while all plants in group 2 showed severe wilt.

After the treatment period, attempts were made to re-isolate virulent bacterial strain *E.a.* 6-4 from the treated seedlings. 5 seedlings from each group were cut in two stem sections (top and bottom). Stem samples from each section (middle and bottom) were surface sterilized, plated on nutrient media and incubated at 27° C. The results are set out below in Table 2:

TABLE 2

| | No. of sections producing bacteria | |
|---|---|---|
| Group Number | Middle Stem Section | Bottom Stem Section |
| Group 1 | 1 | 1 |
| Group 2 | 5 | 5 |
| Group 3 | 5 | 2 |
| Group 4: | 0 | 0 |

To conclusively established that group 4 seedlings were infected with the virulent fire bight strain, surface sterilized plant samples were kept on a shaker over night in standard liquid bacteria medium. DNA was extracted from the samples and subjected to PCR amplification for the 16S-23S intergenic spacer (ITS) for the virulent strain. The PCR experiment established that the seedlings of Group 4 were infected with the virulent strain, but the plant's defence mechanisms suppressed massive bacteria growth and symptom development when compared to the control with the virulent strain.

8. Materials and Methods (a) Isolates and Culture Conditions

An isolate of *O. ulmi* was maintained on malt agar slants at −20° C. for long-term storage. To prepare mycelium for DNA extractions, the isolate was sub-cultured for 7 days on modified Salemink medium containing 2% bacto-agar to form colonies. Mycelial disks, 5×5 mm in diameter, were then excised from the periphery of the colony and transferred into 125 mL Erlenmeyer flasks containing 50 mL of liquid modified Salesmink medium and incubated on a rotary shaker (150 rpm) at 25° C. for 6 days to obtain budding yeast-phase cells. Budding yeast-phase cells were harvested by centrifugation at 1,110×g for 20 min. and lyophilized in a Labconco freeze dryer for 2 days.

(b) DNA Extraction, PCR Amplification and Cloning

Genomic DNA was extracted from lyophilized budding phase cells using DNeasy Plant Mini Kit (QIAGEN Inc., CA 91355) as described by the supplier. Specific oligonucleotide primers derived from amino acid sequences were designed and used for PCR amplification.

Each PCR reaction contained 50 pmol of each primer, 50–100 ng of genomic DNA, 10 mM Tris-HCl, 1.5 mM MgCl2, 0.01% gelatin, 0.1% Triton X-100, 1 unit of Taq DNA polymerase, 50 mM KCl and 200 μM each of dATP, dCTP, dGTP and dTTP in a final volume of 50 μL. Amplification was performed under mineral oil in a thermal cycler (BIO/CAN) with the following cycle program: (1) 95° C. for 3 min, (2) 35 times of (a) 95° C. for 1 min, (b) 50° C. for 50 s, (c) 72° C. for 50 s, and (3) 72° C. for 8 min.

An aliquot of 3–5 μL of the PCR product from each reaction was cloned into the TA cloning vector, pCRII (Invitrogen, San Diego, Calif. 92121, USA) following the manufacturer's instruction. Plasmid DNA containing PCR amplified product was verified by Eco RI restriction digestion.

(c) DNA Sequencing

DNA sequencing was performed using double-stranded PCR derived DNA which was sub-cloned into the plasmid vector pCRII. Sequence reactions were carried out with a T7 Sequencing kit (Pharmacia) using S[35] radiolabelled dATP and electrophoresized in a model S2 sequencing gel electrophoresis apparatus (Gibco BRL, life technologies). The universal and reverse primers were used as sequencing primer to determine the DNA sequence.

Although the invention has been described in connection with certain preferred embodiments, it is not intended to be limited thereto. Rather, it is intended that the invention cover all alternate embodiments as may be within the scope of the following claims. The invention also includes all embodiments which are functional equivalents of the specific embodiments and features which have been described herein.

It will be further understood that, although various features of the invention have been described with respect to one or another of the embodiments of the invention, the various features and embodiments of the invention may be combined or used in conjunction with other features and embodiments of the invention as described herein.

SEQUENCE LISTING

```
<160> NUMBER OF SEQ ID NOS: 16

<210> SEQ ID NO 1
<211> LENGTH: 33
<212> TYPE: PRT
<213> ORGANISM: Ophiostoma ulmi sensu lato
<220> FEATURE:
<221> NAME/KEY: VARIANT
<222> LOCATION: (18)
<223> OTHER INFORMATION: Wherein     Xaa at res. 18 = (His or Ser)
<220> FEATURE:
<221> NAME/KEY: VARIANT
<222> LOCATION: (23)
<223> OTHER INFORMATION: wherein     Xaa at res. 23 = (Tyr or Arg)
<220> FEATURE:
<221> NAME/KEY: VARIANT
<222> LOCATION: (27)
<223> OTHER INFORMATION: wherein     Xaa at res. 27 = (Asp or Val)
<220> FEATURE:
<221> NAME/KEY: VARIANT
<222> LOCATION: (30)
<223> OTHER INFORMATION: wherein     Xaa at res. 30 = (Thr or Lys)
<220> FEATURE:
<221> NAME/KEY: VARIANT
<222> LOCATION: (31)
<223> OTHER INFORMATION: wherein     Xaa at res. 31 = (Lys, Gly or Thr)
<220> FEATURE:
<221> NAME/KEY: VARIANT
<222> LOCATION: (32)
<223> OTHER INFORMATION: wherein     Xaa at res. 32 = (Thr or Gly)

<400> SEQUENCE: 1

Ala Glu Pro Val Phe Ala Val Ser Asn Phe Gln Ala Gly Cys Ile Pro
  1               5                  10                  15

His Xaa Ser Gln Gln Arg Xaa Tyr Phe Asp Xaa Val Lys Xaa Xaa Xaa
             20                  25                  30

Gly

<210> SEQ ID NO 2
<211> LENGTH: 23
<212> TYPE: PRT
<213> ORGANISM: Ophiostoma ulmi sensu lato
<220> FEATURE:
<221> NAME/KEY: VARIANT
<222> LOCATION: (17)
<223> OTHER INFORMATION: wherein     Xaa at res. 17 = (Ala or Val)
<220> FEATURE:
<221> NAME/KEY: VARIANT
<222> LOCATION: (22)
<223> OTHER INFORMATION: wherein     Xaa at res. 22 = (Tyr or Ile)
<220> FEATURE:
<221> NAME/KEY: VARIANT
<222> LOCATION: (23)
<223> OTHER INFORMATION: wherein     Xaa at res. 23 = (Ala or Pro)

<400> SEQUENCE: 2

```
Leu Val Ser Gly Ala Thr Trp Gln Val Ser Tyr Gly Asp Gly Arg Tyr
 1               5                  10                  15

Xaa Ile Gln Val Ile Xaa Xaa
            20
```

<210> SEQ ID NO 3
<211> LENGTH: 23
<212> TYPE: PRT
<213> ORGANISM: Ophiostoma ulmi sensu lato

<400> SEQUENCE: 3

```
Val Ser Ser Ser Phe Thr Ser Asp Ser Ser Ile Asp Gly Leu Val Gly
 1               5                  10                  15

Leu Gly Phe Asp Ser Leu Asn
            20
```

<210> SEQ ID NO 4
<211> LENGTH: 10
<212> TYPE: PRT
<213> ORGANISM: Ophiostoma ulmi sensu lato

<400> SEQUENCE: 4

```
Lys Ala Ala Phe Val Val Phe Asp Gly Arg
 1               5                  10
```

<210> SEQ ID NO 5
<211> LENGTH: 687
<212> TYPE: DNA
<213> ORGANISM: Ophiostoma ulmi sensu lato
<220> FEATURE:
<221> NAME/KEY: CDS
<222> LOCATION: (1)..(69)
<220> FEATURE:
<221> NAME/KEY: CDS
<222> LOCATION: (656)..(685)

<400> SEQUENCE: 5

```
gtg tct tct tcc ttc acc tcc gac agc tcc atc gat ggc ctc gtc ggt      48
Val Ser Ser Ser Phe Thr Ser Asp Ser Ser Ile Asp Gly Leu Val Gly
 1               5                  10                  15 ctg ggc ttc gac agc ctc aac tccgcctccc ccagcgctgt tcccactttc         99
Leu Gly Phe Asp Ser Leu Asn
            20
ttcgacaaca tcattggtag cctggacaag cccgttttca ctgctgattt gaagcacaac   159
aagggtaagt actgcctttt cttgaaccta tccaccaaag aataacccat taactcctct   219
tattagccgg ttcatacgac ttcggtgtta tcgacagctc caagtacacc ggcgcccaga   279
cctacgttcc tgttaacacc gaccccggtt actggacatt cacctcgtct ggctacggaa   339
ttggaactgc tgctttcaag tccactagcg tcactggtat tgccgatacc ggtactaccc   399
tgctgtacct cgacaccgcc atcgtcaagg cctactacgc acagatcagc ggttcgtcca   459
acagcgctac tacggtggct acgtttttcaa gtgctctgcc acccccctg atttacttcg   519 gtgtcggcag tgccacaatt actatccccg gtagctacat taactacggc cccgtcactc   579
cggcagcacc acttgcttcg gcggtctgca ggacagctcg gatattggca tcaacatctt   639
tggcgatgtt gcccctt aag gct gcg ttc gtt gtt ttc gac gga agg gc       687
                  Lys Ala Ala Phe Val Val Phe Asp Gly Arg
                   25                  30
```

<210> SEQ ID NO 6
<211> LENGTH: 33
<212> TYPE: PRT

-continued

```
<213> ORGANISM: Ophiostoma ulmi sensu lato

<400> SEQUENCE: 6

Val Ser Ser Ser Phe Thr Ser Asp Ser Ser Ile Asp Gly Leu Val Gly
 1               5                  10                  15

Leu Gly Phe Asp Ser Leu Asn Lys Ala Ala Phe Val Val Phe Asp Gly
             20                  25                  30
Arg

<210> SEQ ID NO 7
<211> LENGTH: 23
<212> TYPE: PRT
<213> ORGANISM: Ophiostoma ulmi sensu lato

<400> SEQUENCE: 7

Val Ser Ser Ser Phe Thr Ser Asp Ser Ser Ile Asp Gly Leu Val Gly
 1               5                  10                  15

Leu Gly Phe Asp Ser Leu Asn
             20

<210> SEQ ID NO 8
<211> LENGTH: 10
<212> TYPE: PRT
<213> ORGANISM: Ophiostoma ulmi sensu lato

<400> SEQUENCE: 8

Lys Ala Ala Phe Val Val Phe Asp Gly Arg
 1               5                  10

<210> SEQ ID NO 9
<211> LENGTH: 985
<212> TYPE: DNA
<213> ORGANISM: Ophiostoma ulmi sensu lato
<220> FEATURE:
<221> NAME/KEY: CDS
<222> LOCATION: (298)..(366)
<220> FEATURE:
<221> NAME/KEY: CDS
<222> LOCATION: (954)..(983)

<400> SEQUENCE: 9
ggttccgcgg tggctactcc atccctgtca gattggtacc cctgcccagg ttctgaactt      60
gacttggaca ctggctcgtc tgatctatgg gtcttcagca gccttactcc ttcgtctgag     120
gtcaatggcc aatcggtcta cactcctacg aagagcacca cctccaagct agtctctggc     180
gccacctggc aggtctccta tggcgatggc tcgtcgtcca gtggtgtcat ctacactgac     240
aaggtcacca ttggcggcat cactgctgcc agccaggctg ttgaggctgc caaggtt        297 gtt tct tct tcc ttc acc tcc gac agc tcc atc gat ggc ctc gtc ggt      345
Val Ser Ser Ser Phe Thr Ser Asp Ser Ser Ile Asp Gly Leu Val Gly
 1               5                  10                  15 ctg ggc ttc gac agc ctc aac tccgcctccc ccagcgctgt tcccactttc          396
Leu Gly Phe Asp Ser Leu Asn
             20 ttcgacaaca tcattggtag cctggacaag cccgttttca ctgctgattt gaagcacaac     456 aagggtaagt actgccttttt cttgaaccta tccaccaaag aataacccat taactcctct    516 tattagccgg ttcatacgac ttcggtgtta tcgacagctc caagtacacc ggcgcccaga     576 cctacgttcc tgttaacacc gaccccggtt actggacatt cacctcgtct ggctacggaa     636 ttggaactgc tgctttcaag tccactagcg tcactggtat tgccgatacc ggtactaccc     696
```

```
tgctgtacct cgacaccgcc atcgtcaagg cctactacgc acagatcagc ggttcgtcca    756
acagcgctac tacggtggct acgttttcaa gtgctctgcc accccccctg atttacttcg    816
gtgtcggcag tgccagaatt actatccccg gtagctacat taactacggg ccccgtcact    876
ccggcagcac cacttgcttc ggcggtctgc aggacagctc ggatattggc atcaacatct    936
ttggcgatgt tgcccctt aag gct gcg ttc gtt gtt ttc gac gga agg gc      985
                    Lys Ala Ala Phe Val Val Phe Asp Gly Arg
                                 25                 30
```

<210> SEQ ID NO 10
<211> LENGTH: 33
<212> TYPE: PRT
<213> ORGANISM: Ophiostoma ulmi sensu lato

<400> SEQUENCE: 10

```
Val Ser Ser Ser Phe Thr Ser Asp Ser Ser Ile Asp Gly Leu Val Gly
  1               5                  10                  15

Leu Gly Phe Asp Ser Leu Asn Lys Ala Ala Phe Val Val Phe Asp Gly
             20                  25                  30

Arg
```

<210> SEQ ID NO 11
<211> LENGTH: 23
<212> TYPE: PRT
<213> ORGANISM: Ophiostoma ulmi sensu lato

<400> SEQUENCE: 11

```
Val Ser Ser Ser Phe Thr Ser Asp Ser Ser Ile Asp Gly Leu Val Gly
  1               5                  10                  15

Leu Gly Phe Asp Ser Leu Asn
             20
```

<210> SEQ ID NO 12
<211> LENGTH: 10
<212> TYPE: PRT
<213> ORGANISM: Ophiostoma ulmi sensu lato

<400> SEQUENCE: 12

```
Lys Ala Ala Phe Val Val Phe Asp Gly Arg
  1               5                  10
```

<210> SEQ ID NO 13
<211> LENGTH: 985
<212> TYPE: DNA
<213> ORGANISM: Ophiostoma ulmi sensu lato
<220> FEATURE:
<221> NAME/KEY: CDS
<222> LOCATION: (1)..(459)
<220> FEATURE:
<221> NAME/KEY: intron
<222> LOCATION: (461)..(603)
<220> FEATURE:
<221> NAME/KEY: misc_recomb
<222> LOCATION: (460)..(604)
<220> FEATURE:
<221> NAME/KEY: CDS
<222> LOCATION: (603)..(983)

<400> SEQUENCE: 13

```
ggt tcc gcg gtg gct act cca tcc ctg tca gat tgg tac ccc tgc cca     48
Gly Ser Ala Val Ala Thr Pro Ser Leu Ser Asp Trp Tyr Pro Cys Pro
  1               5                  10                  15 ggt tct gaa ctt gac ttg gac act ggc tcg tct gat cta tgg gtc ttc     96
Gly Ser Glu Leu Asp Leu Asp Thr Gly Ser Ser Asp Leu Trp Val Phe
```

```
              20                  25                  30
agc agc ctt act cct tcg tct gag gtc aat ggc caa tcg gtc tac act    144
Ser Ser Leu Thr Pro Ser Ser Glu Val Asn Gly Gln Ser Val Tyr Thr
         35                  40                  45 cct acg aag agc acc acc tcc aag cta gtc tct ggc gcc acc tgg cag    192
Pro Thr Lys Ser Thr Thr Ser Lys Leu Val Ser Gly Ala Thr Trp Gln
 50                  55                  60 gtc tcc tat ggc gat ggc tcg tcg tcc agt ggt gtc atc tac act gac    240
Val Ser Tyr Gly Asp Gly Ser Ser Ser Ser Gly Val Ile Tyr Thr Asp
 65                  70                  75                  80 aag gtc acc att ggc ggc atc act gct gcc agc cag gct gtt gag gct    288
Lys Val Thr Ile Gly Gly Ile Thr Ala Ala Ser Gln Ala Val Glu Ala
                 85                  90                  95 gcc aag gtt gtt tct tct tcc ttc acc tcc gac agc tcc atc gat ggc    336
Ala Lys Val Val Ser Ser Ser Phe Thr Ser Asp Ser Ser Ile Asp Gly
             100                 105                 110 ctc gtc ggt ctg ggc ttc gac agc ctc aac tcc gcc tcc ccc agc gct    384
Leu Val Gly Leu Gly Phe Asp Ser Leu Asn Ser Ala Ser Pro Ser Ala
         115                 120                 125 gtt ccc act ttc ttc gac aac atc att ggt agc ctg gac aag ccc gtt    432
Val Pro Thr Phe Phe Asp Asn Ile Ile Gly Ser Leu Asp Lys Pro Val
 130                 135                 140 ttc act gct gat ttg aag cac aac aag ggtaagtact gccttttctt          479
Phe Thr Ala Asp Leu Lys His Asn Lys
145                 150 gaacctatcc accaaagaat aacccattaa ctcctcttat tagccggttc atacgacttc  539
ggtgttatcg acagctccaa gtacaccggc gcccagacct acgttcctgt taacaccgac  599 ccc ggt tac tgg aca ttc acc tcg tct ggc tac gga att gga act gct    647
    Gly Tyr Trp Thr Phe Thr Ser Ser Gly Tyr Gly Ile Gly Thr Ala
             155                 160                 165 gct ttc aag tcc act agc gtc act ggt att gcc gat acc ggt act acc    695
Ala Phe Lys Ser Thr Ser Val Thr Gly Ile Ala Asp Thr Gly Thr Thr
     170                 175                 180 ctg ctg tac ctc gac acc gcc atc gtc aag gcc tac tac gca cag atc    743
Leu Leu Tyr Leu Asp Thr Ala Ile Val Lys Ala Tyr Tyr Ala Gln Ile
185                 190                 195                 200 agc ggt tcg tcc aac agc gct act acg gtg gct acg ttt tca agt gct    791
Ser Gly Ser Ser Asn Ser Ala Thr Thr Val Ala Thr Phe Ser Ser Ala
             205                 210                 215 ctg cca ccc ccc ctg att tac ttc ggt gtc ggc agt gcc aga att act    839
Leu Pro Pro Pro Leu Ile Tyr Phe Gly Val Gly Ser Ala Arg Ile Thr
         220                 225                 230 atc ccc ggt agc tac att aac tac ggg ccc cgt cac tcc ggc agc acc    887
Ile Pro Gly Ser Tyr Ile Asn Tyr Gly Pro Arg His Ser Gly Ser Thr
     235                 240                 245 act tgc ttc ggc ggt ctg cag gac agc tcg gat att ggc atc aac atc    935
Thr Cys Phe Gly Gly Leu Gln Asp Ser Ser Asp Ile Gly Ile Asn Ile
 250                 255                 260 ttt ggc gat gtt gcc ctt aag gct gcg ttc gtt gtt ttc gac gga agg    983
Phe Gly Asp Val Ala Leu Lys Ala Ala Phe Val Val Phe Asp Gly Arg
265                 270                 275                 280 gc                                                                 985
```

<210> SEQ ID NO 14
<211> LENGTH: 280
<212> TYPE: PRT
<213> ORGANISM: Ophiostoma ulmi sensu lato

<400> SEQUENCE: 14

Gly Ser Ala Val Ala Thr Pro Ser Leu Ser Asp Trp Tyr Pro Cys Pro
1               5                   10                  15

Gly Ser Glu Leu Asp Leu Asp Thr Gly Ser Ser Asp Leu Trp Val Phe
            20                  25                  30

Ser Ser Leu Thr Pro Ser Ser Glu Val Asn Gly Gln Ser Val Tyr Thr
            35                  40                  45

Pro Thr Lys Ser Thr Thr Ser Lys Leu Val Ser Gly Ala Thr Trp Gln
50                  55                  60

Val Ser Tyr Gly Asp Gly Ser Ser Ser Gly Val Ile Tyr Thr Asp
65                  70                  75                  80

Lys Val Thr Ile Gly Gly Ile Thr Ala Ala Ser Gln Ala Val Glu Ala
                85                  90                  95

Ala Lys Val Val Ser Ser Phe Thr Ser Asp Ser Ser Ile Asp Gly
            100                 105                 110

Leu Val Gly Leu Gly Phe Asp Ser Leu Asn Ser Ala Ser Pro Ser Ala
            115                 120                 125

Val Pro Thr Phe Phe Asp Asn Ile Ile Gly Ser Leu Asp Lys Pro Val
            130                 135                 140

Phe Thr Ala Asp Leu Lys His Asn Lys Gly Tyr Trp Thr Phe Thr Ser
145                 150                 155                 160

Ser Gly Tyr Gly Ile Gly Thr Ala Ala Phe Lys Ser Thr Ser Val Thr
                165                 170                 175

Gly Ile Ala Asp Thr Gly Thr Thr Leu Leu Tyr Leu Asp Thr Ala Ile
                180                 185                 190

Val Lys Ala Tyr Tyr Ala Gln Ile Ser Gly Ser Ser Asn Ser Ala Thr
        195                 200                 205

Thr Val Ala Thr Phe Ser Ser Ala Leu Pro Pro Leu Ile Tyr Phe
    210                 215                 220

Gly Val Gly Ser Ala Arg Ile Thr Ile Pro Gly Ser Tyr Ile Asn Tyr
225                 230                 235                 240

Gly Pro Arg His Ser Gly Ser Thr Thr Cys Phe Gly Gly Leu Gln Asp
                245                 250                 255

Ser Ser Asp Ile Gly Ile Asn Ile Phe Gly Asp Val Ala Leu Lys Ala
            260                 265                 270

Ala Phe Val Val Phe Asp Gly Arg
            275                 280

<210> SEQ ID NO 15
<211> LENGTH: 153
<212> TYPE: PRT
<213> ORGANISM: Ophiostoma ulmi sensu lato

<400> SEQUENCE: 15

Gly Ser Ala Val Ala Thr Pro Ser Leu Ser Asp Trp Tyr Pro Cys Pro
1               5                   10                  15

Gly Ser Glu Leu Asp Leu Asp Thr Gly Ser Ser Asp Leu Trp Val Phe
            20                  25                  30

Ser Ser Leu Thr Pro Ser Ser Glu Val Asn Gly Gln Ser Val Tyr Thr
            35                  40                  45

Pro Thr Lys Ser Thr Thr Ser Lys Leu Val Ser Gly Ala Thr Trp Gln
        50                  55                  60

Val Ser Tyr Gly Asp Gly Ser Ser Ser Gly Val Ile Tyr Thr Asp
65                  70                  75                  80

Lys Val Thr Ile Gly Gly Ile Thr Ala Ala Ser Gln Ala Val Glu Ala

-continued

```
                85                  90                  95

Ala Lys Val Val Ser Ser Ser Phe Thr Ser Asp Ser Ser Ile Asp Gly
            100                 105                 110

Leu Val Gly Leu Gly Phe Asp Ser Leu Asn Ser Ala Ser Pro Ser Ala
        115                 120                 125

Val Pro Thr Phe Phe Asp Asn Ile Ile Gly Ser Leu Asp Lys Pro Val
    130                 135                 140

Phe Thr Ala Asp Leu Lys His Asn Lys
145                 150

<210> SEQ ID NO 16
<211> LENGTH: 127
<212> TYPE: PRT
<213> ORGANISM: Ophiostoma ulmi sensu lato

<400> SEQUENCE: 16

Gly Tyr Trp Thr Phe Thr Ser Ser Gly Tyr Gly Ile Gly Thr Ala Ala
  1               5                  10                  15

Phe Lys Ser Thr Ser Val Thr Gly Ile Ala Asp Thr Gly Thr Thr Leu
            20                  25                  30

Leu Tyr Leu Asp Thr Ala Ile Val Lys Ala Tyr Tyr Ala Gln Ile Ser
        35                  40                  45

Gly Ser Ser Asn Ser Ala Thr Thr Val Ala Thr Phe Ser Ser Ala Leu
    50                  55                  60

Pro Pro Pro Leu Ile Tyr Phe Gly Val Gly Ser Ala Arg Ile Thr Ile
 65                  70                  75                  80

Pro Gly Ser Tyr Ile Asn Tyr Gly Pro Arg His Ser Gly Ser Thr Thr
                85                  90                  95

Cys Phe Gly Gly Leu Gln Asp Ser Ser Asp Ile Gly Ile Asn Ile Phe
            100                 105                 110

Gly Asp Val Ala Leu Lys Ala Ala Phe Val Val Phe Asp Gly Arg
        115                 120                 125
```

I claim:

1. A method for inducing resistance to a wilt disease other than Dutch Elm Disease in a woody perennial plant, comprising administering to the woody perennial plant a glycoprotein elicitor in an amount sufficient to cause a defense reaction in the plant.

2. The method of claim 1, wherein the elicitor is obtainable from a Dutch Elm Disease-causing fungus.

3. The method of claim 2 wherein the plant is a tree.

4. The method of claim 3, wherein the tree is a fruit tree.

5. The method of claim 3, wherein the tree is selected from the group comprising the family Rosaceae.

6. The method of claim 3, wherein the tree is selected from the group comprising Malus and Pyrus.

7. The method of claim 3, wherein the elicitor is obtainable from the cell interior, cell wall or culture filtrate of a Dutch Elm Disease-causing fungus.

8. The method of claim 7, wherein the Dutch Elm Disease-causing fungus is *Ophiostoma ulmi.*

9. The method of claim 8, wherein the Dutch Elm Disease-causing fungus is a non-aggressive strain of *Ophiostoma ulmi.*

10. The method of claim 9, wherein the elicitor is a glycoprotein obtained from a culture filtrate of *Ophiostoma ulmi* strain Q412, and comprises at least one amino acid sequence selected from the group consisting of SEQ ID NO. 1, SEQ ID NO. 2, SEQ ID NO. 3, SEQ ID NO. 4, SEQ ID NO. 15 and SEQ ID NO. 16.

11. The method of claim 10, wherein the elicitor has a molecular weight of at least 21 kDa.

12. The method of claim 11, wherein SEQ. ID NO. 1 begins at the N-terminal of the amino acid sequence of the elicitor.

13. The method of claim 3, wherein the amount of elicitor effective to cause the tree to exhibit a defense reaction is from about 0.1 mg to about 150 mg.

14. The method of claim 3, wherein the elicitor is administered to the vascular system of the tree.

15. The method of claim 3, wherein the administering of the elicitor to the tree comprises injection of a liquid composition containing the elicitor into the tree.

16. The method of claim 15, wherein the liquid composition comprises an aqueous solution of the elicitor.

17. The method of claim 16, wherein the elicitor is present in the solution in a concentration of from about 0.1 mg/mL to about 50 mg/mL.

18. The method of claim 17, wherein the injection delivers the liquid composition inside the vascular system adjacent to the bark of the tree.

19. The method of claim 3, wherein the administering of the elicitor to the tree comprises insertion of the elicitor in a solid form into the tree.

20. The method of claim 19, wherein the solid form of the elicitor comprises a solid composition comprising the elicitor, the solid composition being contained in a capsule.

21. The method of claim 20, wherein the composition additionally comprises acceptable fillers and carriers.

22. The method of claim 21, wherein insertion of the elicitor into the tree comprises drilling a hole through the bark of the tree, and inserting the capsule into the hole so that the elicitor is received inside the vascular system adjacent to the bark of the tree.

23. The method of claim 3, wherein the administering of the elicitor to the tree comprises spraying of a liquid composition containing the elicitor while the tree is flowering.

24. The method of claim 23, wherein the liquid composition comprises an aqueous solution of the elicitor.

25. The method of claim 24, wherein the elicitor is present in the solution in a concentration of from about 0.1 mg/mL to about 50 mg/mL.

26. The method of claim 2, wherein the defense reaction comprises accumulation of growth inhibitory compounds in tissue of the tree.

27. The method of claim 3, wherein the disease is Fire Blight Disease and the tree is a Fire Blight Disease susceptible tree.

28. The method of claim 4, wherein the disease is Fire Blight Disease and the tree is a Fire Blight Disease susceptible tree.

29. The method of claim 5, wherein the disease is Fire Blight Disease and the tree is a Fire Blight Disease susceptible tree.

30. The method of claim 6, wherein the disease is Fire Blight Disease and the tree is a Fire Blight Disease susceptible tree.

31. The method of claim 10, wherein the disease is Fire Blight Disease and the tree is a Fire Blight Disease susceptible tree.

32. The method of claim 31, wherein the elicitor has a molecular weight of at least 21 kDa.

33. The method of claim 32, wherein SEQ. ID NO. 1 begins at the N-terminal of the amino acid sequence of the elicitor.

34. A method for introducing resistance to a wilt disease other than Dutch Elm Disease in a woody perennial plant, comprising administering to the plant a glycoprotein in an amount sufficient to cause a defense reaction in the plant, the glycoprotein comprising at least one amino acid sequence selected from the group consisting of SEQ. ID NO. 1, SEQ. ID NO. 2, SEQ. ID NO.3, SEQ. ID NO. 4, SEQ. ID NO. 15 and SEQ. ID NO. 16.

35. The method of claim 34, wherein the elicitor is obtainable from a Dutch Elm Disease-causing fungus.

36. The method of claim 35, wherein the plant is a tree.

37. The method of claim 36 wherein the disease is Fire Blight Disease.

38. The method of claim 37, wherein the tree is a fruit tree.

39. The method of claim 37, wherein the tree is selected from the group comprising the family Rosaceae.

40. The method of claim 37, wherein the tree is selected from the group comprising Malus and Pyrus.

41. The method of claim 35, wherein the glycoprotein has a molecular weight of at least 21 kDa.

42. The method of claim 41, wherein SEQ. ID NO. 1 begins at the N-terminal of the amino acid sequence glycoprotein.

43. The method of claim 35, wherein the defense reaction comprises accumulation of growth inhibitory compounds in tissue of the plant.

* * * * *